United States Patent
Wan et al.

(10) Patent No.: US 11,840,504 B2
(45) Date of Patent: Dec. 12, 2023

(54) METHOD FOR PREPARING PERFLUOROALKYL SULFINATE ESTER

(71) Applicant: SOOCHOW UNIVERSITY, Suzhou (CN)

(72) Inventors: Xiaobing Wan, Suzhou (CN); Hanghang Wang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 435 days.

(21) Appl. No.: 17/205,937

(22) Filed: Mar. 18, 2021

(65) Prior Publication Data

US 2021/0221769 A1 Jul. 22, 2021

Related U.S. Application Data

(63) Continuation of application No. PCT/CN2018/106582, filed on Sep. 19, 2018.

(51) Int. Cl.
*C07C 313/04* (2006.01)

(52) U.S. Cl.
CPC .................. *C07C 313/04* (2013.01)

(58) Field of Classification Search
CPC .................................................. C07C 313/04
See application file for complete search history.

(56) References Cited

U.S. PATENT DOCUMENTS 4,489,091 A 12/1984 Fujii et al.

FOREIGN PATENT DOCUMENTS

| CN | 102414173 A | 4/2012 |
| CN | 106518734 A | 3/2017 |

OTHER PUBLICATIONS

Vedejs et al., J. Org. Chem., 42(19), 1977, 3109-3113.*
Wang et al., Chem. Eur. J., 2019, 25, 2195-2198.*
Joh-Gyu Hahn et al., "Base-Catalyzed Rearrangement of Some 1,3-Oxathiolane Sulfoxides: Mechanistic Viewpoint of the Sigmatropic and Elimination Reactions" Bull. Korean Chem. Soc. 2004, vol. 25, No. 9, pp. 1379-1384 (Dec. 31, 2001).
Eugeniy T. Satumov et al., "Protonation and transformations of a-diazo-b-dicarbonyl compounds in superacids: generation of the strongest carbon-centered cationic electrophiles at the protonation of diazomalonates in FriedeleCrafts reactions" Tetrahedron 72 (2016) 4835-4844 (Jun. 27, 2016).

* cited by examiner

*Primary Examiner* — Sun Jae Yoo
(74) *Attorney, Agent, or Firm* — SZDC LAW P.C.

(57) ABSTRACT

The present invention discloses a method for preparing a perfluoroalkyl sulfinate ester. The method includes reacting an α-carbonyldiazo compound and a sodium perfluoroalkyl sulfinate, in an organic solvent, in the presence of anhydrous copper acetate as an optimal catalyst and tert-butyl hydroperoxide (TBHP) as a green oxidant, to obtain the perfluoroalkyl sulfinate ester. Compared to the prior art, the present method has the advantages of a wide range of reaction substrates, a short reaction time, a high reaction yield, and mild reaction conditions. The reaction does not require pre-activation of sodium perfluoroalkyl sulfinate, which can participate in the reaction directly, making reaction operations simple. The present method uses TBHP as a green oxidant and produces tert-butanol and water after reaction. Moreover, the present method avoids using a bromide or a chloride as a reaction material, and thus avoids formation of a large amount of a halide salt.

5 Claims, No Drawings

METHOD FOR PREPARING PERFLUOROALKYL SULFINATE ESTER

This application is a Continuation Application of PCT/CN2018/106582, filed on Sep. 19, 2018, which is incorporated by reference for all purposes as if fully set forth herein.

TECHNICAL FIELD

The invention relates to a method for preparing a perfluoroalkylsulfinate ester, in the technical field of organic synthesis.

BACKGROUND TECHNIQUE

Sulfinate ester is an important intermediate in organic synthesis. Depending on the reaction conditions, it can be used as both an electrophile and a nucleophile. In addition, sulfinate ester also exhibits important biological activities. On the other hand, due to the unique properties of fluorine atoms, the introduction of fluorine-containing groups into organic molecules will significantly change the physical and chemical properties of compounds. These compounds are often used in the fields of medicine, pesticides, and materials science. Therefore, it is particularly important for the synthesis of sulfinate esters having perfluoroalkyl groups. According to literature review, it has been found that there are few reports on the synthesis of sulfinate esters of this kind, and at present, it is limited to the reports of trifluoromethylsulfinate ester. However, these methods have some disadvantages, such as harsh reaction conditions, long reaction time, low yield, narrow substrate range, and a large number of halide by-products. For example:

(1) Trifluoromethyl sulfinate ester is prepared from trifluoromethyl sulfinate and alcohol or phenol. However, trifluoromethylsulfinyl chloride needs to be activated with 2,4,6-trimethylbenzenesulfonyl chloride or phosphorus oxychloride to generate trifluoromethylsulfinyl chloride in situ. This process generates equivalent environmental byproducts, such as sulfonate or chloride;

(2) A trifluoromethylsulfinate ester is prepared by using trifluoromethylsulfonyl chloride and an alcohol substance under the action of equivalent trimethoxyphosphine and triethylamine. This process also pre-activates trifluoromethylsulfonyl chloride to generate trifluoromethylsulfinyl chloride in situ. This process produces equivalent by-products, such as chlorides that pollute the environment;

(3) A corresponding trifluoromethylsulfinate ester is obtained by reacting silver trifluoromethanesulfinate with 1-bromo-3-phenylpropane, acetonitrile as a solvent, and reacting under reflux for 18 hours with a yield of 65%. During the reaction, an equivalent amount of silver bromide by-product is generated, and the reaction time is relatively long;

(4) By using palladium to catalyze the oxidation of amino trifluoromethylsulfinyl in omega-aminoolefin molecules, a trifluoromethylsulfinate ester with special structure is synthesized. However, the reaction yield is relatively low, the substrate range is relatively narrow, and the reaction conditions are relatively harsh. A large amount of acid and t-butoxychloride are used. In addition, iodobenzene acetate andoxidant used in the reaction produced a large amount of iodobenzene by-product.

In summary, the currently reported methods for synthesizing trifluoromethanesulfinate ester have a complicated reaction process, harsh reaction conditions, low yield, long reaction time, and a large number of environmentally harmful halogenated salts by-product. In addition, no literature has been reported on perfluoroalkylsulfinates ester. Therefore, it is particularly important to develop a method with abundant raw materials, high reactivity, low cost, safety, environmental protection, and easy operation for the effective synthesis of perfluoroalkylsulfinate esters.

Technical Problem

The object of the present invention is to provide a method for preparing the perfluoroalkylsulfinate ester, which has abundant sources of reaction raw materials, universal reaction substrates, mild reaction conditions, short reaction time, and simple operation.

Technical Solutions

In order to achieve the above-mentioned objects of the invention, the technical solution adopted by the present invention is:

A method for preparing a perfluoroalkylsulfinate ester includes: conducting a reaction of α-carbonyldiazo compound and sodium perfluoroalkylsulfinate, in the presence of a transition metal compound as a catalyst, and a peroxide base as an oxidant, in an organic solvent, to obtain the perfluoroalkylsulfinate ester. The α-carbonyldiazo compound has the following chemical structural formula:

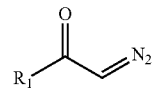

$R_1$ is selected from the group consisting of naphthyl, thienyl, alkyl, alkoxy, and phenol, or R1 has the following chemical structural formula:

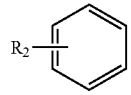

$R_2$ is selected from the group consisting of hydrogen, methyl, ethyl, tert-butyl, methoxy, phenyl, fluorine, chlorine, bromine, trifluoromethyl, hydroxyl, acetoxy, and p-toluenesulfonyloxy;

The sodium perfluoroalkylsulfinate has the following chemical structural formula:

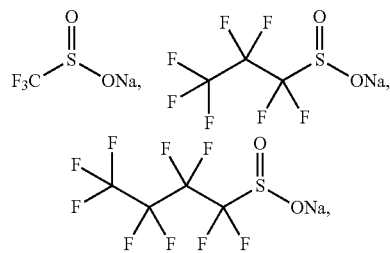

-continued

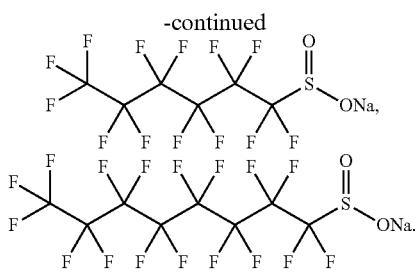

The transition metal compound is selected from the group consisting of a copper compound, a cobalt compound, and an iron compound.

The peroxide is hydrogen peroxide or tert-peroxide.

The perfluoroalkylsulfinate ester has the following chemical structural formula:

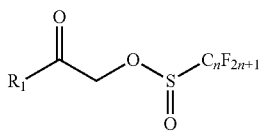

n is 1 to 8, such as 1, 3, 4, 6, 8.

In the above technical solution, the reaction is conducted at 50 to 90° C., for 1 to 6 hours in the air; the transition metal compound is a copper compound; the organic solvent is petroleum ether, 1,2-di chloroethane, 1,1,1-trichloroethane, 1,1,2-trichloroethane, nitro methane, acetonitrile or ethyl acetate.

Preferably, the reaction is conducted at 60° C., for 1 h; and the copper compound is anhydrous copper acetate.

In the above technical solution, an amount of the catalyst is 10 mol % of the α-carbonyldiazo compound, a molar ratio of the oxidant to the α-carbonyldiazo compound is 4-7:1, and a molar ratio of the sodium perfluoroalkylsulfinate to the α-carbonyldiazo compound is 3:1. The oxidant is TBHP, and molar ratio of the oxidant to the α-carbonyldiazo compound is 5:1.

In the above technical solution, after the reaction is complete, the reaction system is diluted with ethyl acetate, then the solvent is removed, and silica gel column chromatograph is carried out to obtain the product perfluoroalkylsulfinate ester.

This invention discloses an application of a transition metal compound as a catalyst and a peroxide as an oxidant in the preparation of a perfluoroalkylsulfinate ester. The transition metal compound is selected from the group consisting of a copper compound, a cobalt compound, and an iron compound. The peroxide is hydrogen peroxide or TBHP.

In the above technical solution, a reaction of α-carbonyldiazo compound and sodium perfluoroalkylsulfinate is conducted in a solvent to prepare the perfluoroalkylsulfinate ester. The α-carbonyldiazo compound has the following chemical structural formula:

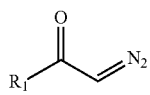

$R_1$ is selected from the group consisting of naphthyl, thienyl, alkyl, alkoxy, and phenol, or $R_1$ has the following chemical structural formula:

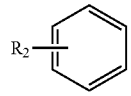

$R_2$ is selected from the group consisting of hydrogen, methyl, ethyl, tert-butyl, methoxy, phenyl, fluorine, chlorine, bromine, trifluoromethyl, hydroxyl, acetoxy, and p-toluenesulfonyloxy;

The sodium perfluoroalkylsulfinate has the following chemical structural formula:

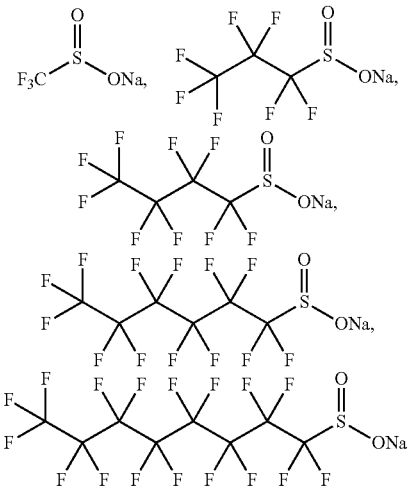

This invention discloses an application of an α-carbonyldiazo compound and sodium perfluoroalkylsulfinate as reaction substrates in the preparation of a perfluoroalkylsulfinate ester.

The α-carbonyldiazo compound has the following chemical structural formula:

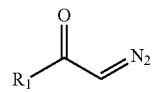

$R_1$ is selected from the group consisting of naphthyl, thienyl, alkyl, alkoxy, and phenol, or $R_1$ has the following chemical structural formula:

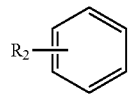

$R_2$ is selected from the group consisting of hydrogen, methyl, ethyl, tert-butyl, methoxy, phenyl, fluorine, chlorine, bromine, trifluoromethyl, hydroxyl, acetoxy, and p-toluenesulfonyloxy;

The sodium perfluoroalkylsulfinate has the following chemical structural formula:

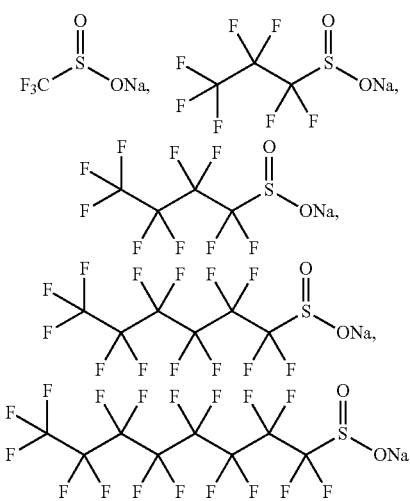

In the above technical solution, the transition metal compound is used as a catalyst and the peroxide base is used as an oxidant to prepare a perfluoroalkylsulfinate ester. The transition metal compound is selected from the group consisting of a copper compound, a cobalt compound, and an iron compound; the peroxide is hydrogen peroxide or TBHP.

In the above technical solution, an amount of the catalyst is 10 mol % of the α-carbonyldiazo compound, a molar ratio of the oxidant to the α-carbonyldiazo compound is 4-7:1, and a molar ratio of the sodium perfluoroalkylsulfinate to the α-carbonyldiazo compound is 3:1. The oxidant is TBHP, and molar ratio of the oxidant to the α-carbonyldiazo compound is 5:1.

This invention discloses a perfluoroalkylsulfinate ester prepared by the methods of the present invention.

The reaction of the present invention is conducted in the air. After the reaction is complete, the reaction system is diluted with ethyl acetate, then the solvent is removed, and silica gel column chromatography is carried out to obtain the product perfluoroalkylsulfinate ester.

Beneficial Effects

With the application of the above technical solutions, the present invention has the following advantages compared with the prior art:
1. The catalyst used in the present invention is copper acetate, which realizes the coupling reaction of a diazo compound with sodium perfluoroalkylsulfinate to prepare a perfluoroalkylsulfinate ester. In the prior at, the reaction substrate is narrow, the reaction time is long, the reaction yield is low, and the reaction conditions are harsh. Compared with prior art, the present invention has the characteristics of a wide range of reaction substrates, short reaction time, high reaction yield, and mild reaction conditions.
2. The technology of the present invention does not require pre-activation treatment of sodium perfluoroalkylsulfinate, and can directly use it in the reaction, thereby avoiding excessively complicated problems in operation and avoiding the use of a large amount of chlorinating reagents.
3. The oxidant used in the technology of the present invention is green oxidant tert-butanol (TBHP), and the by-products produced after the reaction are tert-butanol and water, which is not harmful to the environment.
4. The technology of the present invention uses an α-carbonyldiazo compound as a reaction starting material. Compared with the prior art, the use of brominated or chlorinated compounds as a reaction raw material is avoided. The by-product generated by the reaction is nitrogen, and a large amount of halogenation and formation of salt are avoided during the reaction. Therefore, the technology of the invention has the advantages of environmental friendly and no pollution to the environment.
5. Compared with the prior art, the technology of the present invention can not only prepare trifluoromethylsulfinate ester, but also perfluoropropyl, perfluorobutyl, perfluorohexyl and perfluorooctylsulfinate, which expands the scope of the method.

EXAMPLES OF THE INVENTION

The following further describes the present invention with reference to the examples:

The sodium trifluoromethylsulfinate, the catalyst, the oxidant, and the organic solvent of the present invention are all commercialized products and can be purchased directly. The α-carbonyldiazo compounds can be prepared with corresponding carboxylic acids, alcohols, phenols. The sodium perfluoroalkylsulfinate can be obtained from the corresponding perfluoroiodoalkane and sodium dithionite.

Example 1

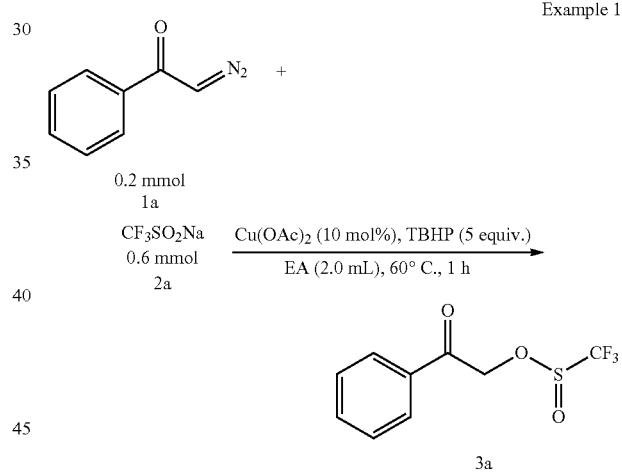

Compound 1a (0.2 mmol, 29.3 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3a, in a yield 75%. The analytical data of the prepared product are as follows. The data of the actual synthetic products are consistent with the theoretical analysis.

$^1$H NMR (400 MHz, CDCl$_3$) δ 7.91-7.89 (m, 2H), 7.68-7.68 (m, 1H), 7.54-7.50 (m, 2H), 5.57 (d, J=16.8 Hz, 1H), 5.38 (d, J=16.8 Hz, 1H). $^{13}$C NMR (100 MHz, CDCl$_3$) δ 191.1, 134.6, 133.1, 129.1, 127.8, 67.8. $^{19}$F NMR (376 MHz, CDCl$_3$) δ −79.0 (s, 3F). HRMS (ESI-TOF): Anal. Calcd. For C$_9$H$_7$F$_3$O$_3$S$^+$ Na$^+$: 274.9960, Found: 274.9935; IR (neat, cm$^{-1}$): ν 2992, 2942, 1686, 1450, 1186, 953, 753, 713, 675.

Example 2

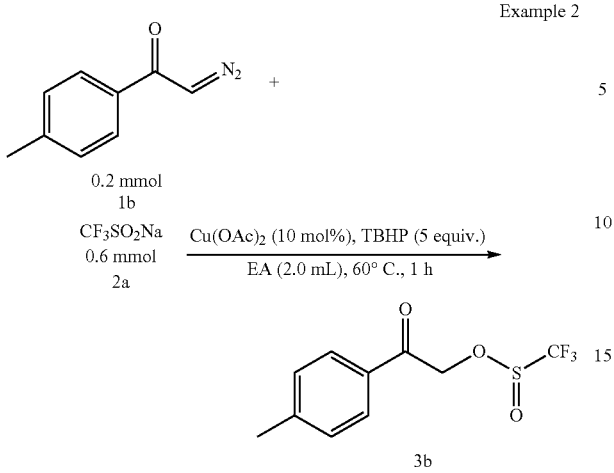

Compound 1b (0.2 mmol, 32.0 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3b, in a yield 61%. The analytical data of the prepared product are as follows. The data of the actual synthetic products are consistent with the theoretical analysis.

$^1$H NMR (400 MHz, CDCl$_3$) δ 7.79 (d, J=8.2 Hz, 2H), 7.31 (d, J=8.0 Hz, 2H), 5.54 (d, J=16.7 Hz, 1H), 5.35 (d, J=16.7 Hz, 1H), 2.44 (s, 3H). $^{13}$C NMR (100 MHz, CDCl$_3$) δ 190.7, 145.9, 130.6, 129.8, 127.9, 67.9, 21.8. $^{19}$F NMR (376 MHz, CDCl$_3$) δ −79.1 (s, 3F). HRMS (ESI-TOF): Anal. Calcd. For C$_{10}$H$_9$F$_3$O$_3$S+Na$^+$: 289.0117, Found: 289.0122; IR (neat, cm$^{-1}$): ν 2992, 2927, 1681, 1604, 1188, 1132, 948, 723.

Example 3

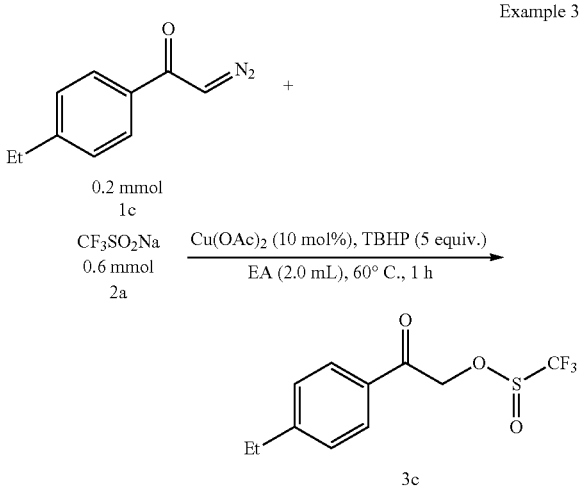

Compound 1c (0.2 mmol, 34.9 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3c, in a yield 64%. The analytical data of the prepared product are as follows. The data of the actual synthetic products are consistent with the theoretical analysis.

$^1$H NMR (400 MHz, CDCl$_3$) δ 7.82 (d, J=8.3 Hz, 2H), 7.34 (d, J=8.3 Hz, 2H), 5.55 (d, J=16.6 Hz, 1H), 5.35 (d, J=16.6 Hz, 1H), 2.73 (q, J=7.6 Hz, 2H), 1.27 (t, J=7.6 Hz, 3H). $^{13}$C NMR (100 MHz, CDCl$_3$) δ 190.7, 152.0, 130.8, 128.6, 128.1, 67.8, 29.1, 15.0. $^{19}$F NMR (376 MHz, CDCl$_3$) δ −79.0 (s, 3F). HRMS (ESI-TOF): Anal. Calcd. For C$_{11}$H$_{11}$F$_3$O$_3$S+Na$^+$: 303.0273, Found: 303.0270; IR (neat, cm$^{-1}$): ν 2972, 2935, 2880, 1681, 1190, 952, 829, 765.

Example 4

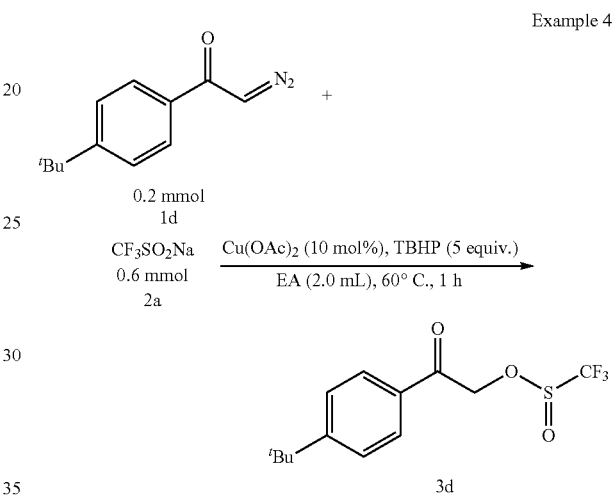

Compound 1d (0.2 mmol, 40.5 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3d, in a yield 61%. The analytical data of the prepared product are as follows. The data of the actual synthetic products are consistent with the theoretical analysis.

$^1$H NMR (400 MHz, CDCl$_3$) δ 7.84 (d, J=8.5 Hz, 2H), 7.53 (d, J=8.5 Hz, 2H), 5.55 (d, J=16.7 Hz, 1H), 5.36 (d, J=16.7 Hz, 1H), 1.35 (s, 9H). $^{13}$C NMR (100 MHz, CDCl$_3$) δ 190.7, 158.8, 130.6, 127.8, 126.1, 67.8, 35.3, 30.9. $^{19}$F NMR (376 MHz, CDCl$_3$) δ −79.0 (s, 3F). HRMS (ESI-TOF): Anal. Calcd. For C$_{13}$H$_{15}$F$_3$O$_3$S+Na$^+$: 331.0586, Found: 331.0582; IR (neat, cm$^{-1}$): ν 2986, 2928, 2870, 1684, 1187, 953, 831, 718.

Example 5

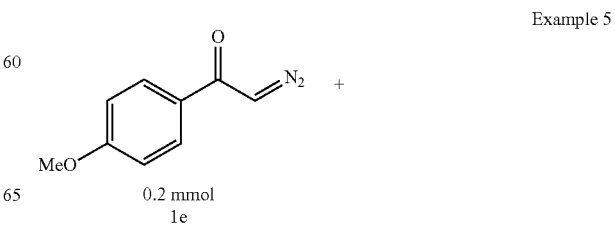

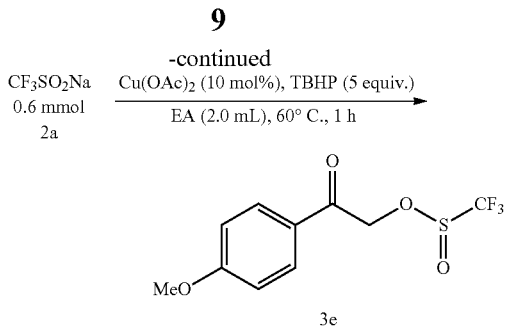

Compound 1e (0.2 mmol, 35.3 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3e, in a yield 56%. The analytical data of the prepared product are as follows. The data of the actual synthetic products are consistent with the theoretical analysis.

$^1$H NMR (400 MHz, CDCl$_3$) δ 7.88 (d, J=8.8 Hz, 2H), 6.98 (d, J=8.8 Hz, 2H), 5.52 (d, J=16.5 Hz, 1H), 5.33 (d, J=16.5 Hz, 1H), 3.89 (s, 3H). $^{13}$C NMR (100 MHz, CDCl$_3$) δ 189.5, 164.7, 130.3, 126.0, 114.3, 67.8, 55.6. $^{19}$F NMR (376 MHz, CDCl$_3$) δ −79.1 (s, 3F). HRMS (ESI-TOF): Anal. Calcd. For C$_{10}$H$_9$F$_3$O$_4$S+Na$^+$: 305.0066, Found: 305.0059; IR (neat, cm$^{-1}$): ν 2974, 2846, 1669, 1181, 1048, 837, 721, 636.

Example 6

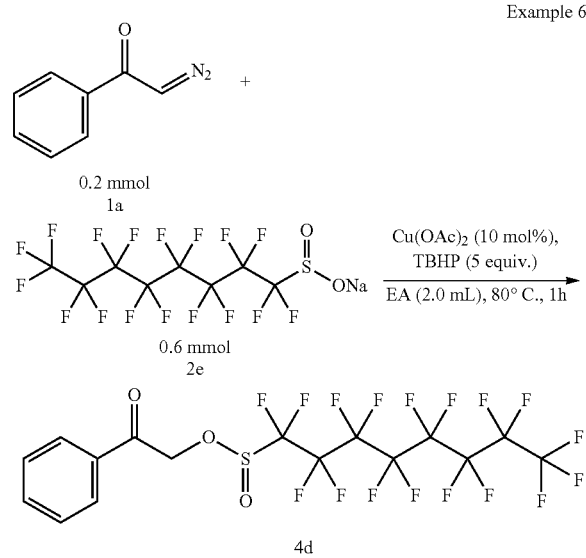

Compound 1a (0.2 mmol, 29.3 mg), 2e (0.6 mmol, 303.7 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 4d, in a yield 70%. The analytical data of the prepared product are as follows. The data of the actual synthetic products are consistent with the theoretical analysis.

$^1$H NMR (400 MHz, CDCl$_3$) δ 7.96-7.86 (m, 2H), 7.68-7.64 (m, 1H), 7.54-7.50 (m, 2H), (d, J=16.6 Hz, 1H), 5.34 (d, J=16.6 Hz, 1H). $^{13}$C NMR (100 MHz, CDCl$_3$) δ 191.0, 134.7, 133.2, 129.1, 127.9, 67.4, not all carbons are reported due to extensive $^{19}$F splitting. $^{19}$F NMR (376 MHz, CDCl$_3$) δ −80.8 (t, J=9.9 Hz, 3F), −119.1--121.0 (m, 2F), −121.2--121.3 (m, 2F), −121.8--121.9 (m, 6F), −122.72--122.73 (m, 2F), −126.11--126.14 (m, 2F). HRMS (ESI-TOF): Anal. Calcd. For C$_{16}$H$_7$F$_{17}$O$_3$S+Na+: 624.9737, Found: 624.9721; IR (neat, cm$^{-1}$): ν 2957, 2923, 2853, 1690, 1199, 959, 720, 687.

Example 7

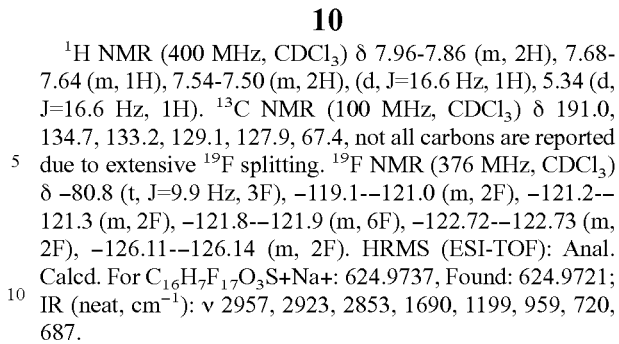

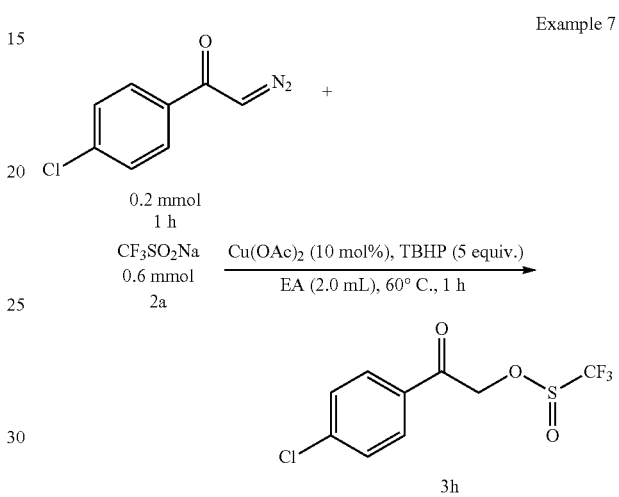

Compound 1h (0.2 mmol, 29.3 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3h, in a yield 71%. The analytical data of the prepared product are as follows. The data of the actual synthetic products are consistent with the theoretical analysis.

$^1$H NMR (400 MHz, CDCl$_3$) δ 7.92-7.77 (m, 2H), 7.51-7.49 (m, 2H), 5.53 (d, J=16.6 Hz, 1H), 5.32 (d, J=16.6 Hz, 1H). $^{13}$C NMR (100 MHz, CDCl$_3$) δ 190.1, 141.3, 131.5, 129.5, 129.3, 67.3. $^{19}$F NMR (376 MHz, CDCl$_3$) δ −78.8 (s, 3F). HRMS (ESI-TOF): Anal. Calcd. For C$_9$H$_6$ClF$_3$O$_3$S+Na$^+$: 308.9570, Found: 308.9582; IR (neat, cm$^{-1}$): ν 3096, 2994, 2853, 1685, 1183, 1091, 951, 814, 703.

Example 8

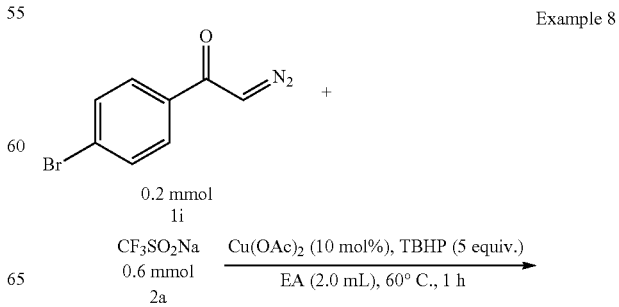

-continued

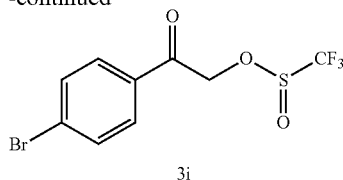

3i

Compound 1i (0.2 mmol, 45.0 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3i, in a yield 63%. The analytical data of the prepared product are as follows. The data of the actual synthetic products are consistent with the theoretical analysis.

$^1$H NMR (400 MHz, CDCl$_3$) δ 7.81-7.73 (m, 2H), 7.72-7.63 (m, 2H), 5.52 (d, J=16.7 Hz, 1H), 5.31 (d, J=16.7 Hz, 1H). $^{13}$C NMR (100 MHz, CDCl$_3$) δ 190.3, 132.5, 131.9, 130.1, 129.3, 67.2. $^{19}$F NMR (376 MHz, CDCl$_3$) δ −78.8 (s, 3F). HRMS (ESI-TOF): Anal. Calcd. For C$_9$H$_6$BrF$_3$O$_3$S+Na$^+$: 352.9065, Found: 352.9071; IR (neat, cm$^{-1}$): ν 3098, 2994, 2853, 1685, 1184, 1070, 951, 816, 708.

Example 9

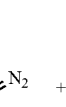

0.2 mmol
1j
CF$_3$SO$_2$Na    Cu(OAc)$_2$ (10 mol%), TBHP (5 equiv.)
0.6 mmol    ——————————————————→
2a              EA (2.0 mL), 60° C., 1 h

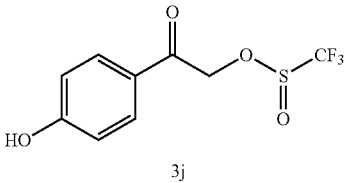

3j

Compound 1j (0.2 mmol, 32.5 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3j, in a yield 63%. The analytical data of the prepared product are as follows. The data of the actual synthetic products are consistent with the theoretical analysis.

$^1$H NMR (400 MHz, DMSO) δ 10.63 (s, 1H), 7.85 (d, J=8.5 Hz, 2H), 6.90 (d, J=8.5 Hz, 2H), 5.94 (d, J=17.4 Hz, 1H), 5.80 (d, J=17.4 Hz, 1H). $^{13}$C NMR (100 MHz, DMSO) δ 191.2, 163.3, 130.8, 124.4, 115.6, 71.8. $^{19}$F NMR (376 MHz, DMSO) δ −79.5 (s, 3F). HRMS (ESI-TOF): Anal. Calcd. For C$_9$H$_7$F$_3$O$_4$S+Na$^+$: 290.9909, Found: 290.9901; IR (neat, cm$^{-1}$): ν 3383, 2993, 2851, 1677, 1172, 1054, 962, 844, 703.

Example 10

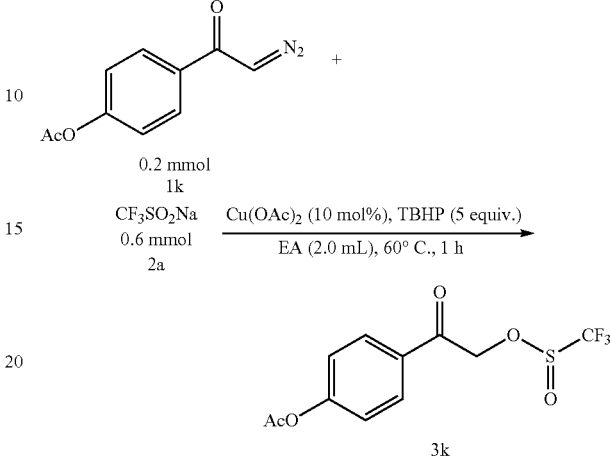

3k

Compound 1k (0.2 mmol, 40.9 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3k, in a yield 57%. The analytical data of the prepared product are as follows. The data of the actual synthetic products are consistent with the theoretical analysis.

$^1$H NMR (400 MHz, CDCl$_3$) δ 7.96-7.88 (m, 2H), 7.28-7.20 (m, 2H), 5.54 (d, J=16.8 Hz, 1H), 5.35 (d, J=16.8 Hz, 1H), 2.33 (s, 3H). $^{13}$C NMR (100 MHz, CDCl$_3$) δ 190.0, 168.6, 155.4, 130.6, 129.5, 122.4, 67.8, 21.0. $^{19}$F NMR (376 MHz, CDCl$_3$) δ −79.0 (s, 3F). HRMS (ESI-TOF): Anal. Calcd. For C$_{11}$H$_9$F$_3$O$_5$S+Na$^+$: 333.0015, Found: 333.0017; IR (neat, cm$^{-1}$): 3109, 2991, 2939, 1751, 1682, 1136, 963, 705, 677.

Example 11

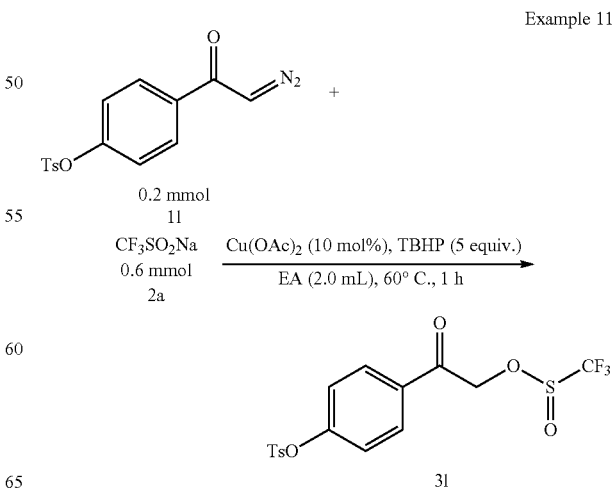

3l

Compound 1l (0.2 mmol, 63.3 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3l, in a yield 73%. The analytical data of the prepared product are as follows. The data of the actual synthetic products are consistent with the theoretical analysis.

$^1$H NMR (400 MHz, CDCl$_3$) δ 7.89-7.82 (m, 2H), 7.71 (d, J=8.2 Hz, 2H), 7.34 (d, J=8.2 Hz, 2H), 7.18-7.12 (m, 2H), 5.52 (d, J=16.8 Hz, 1H), 5.32 (d, J=16.8 Hz, 1H), 2.46 (s, 3H). $^{13}$C NMR (100 MHz, CDCl$_3$) δ 189.9, 153.9, 146.0, 131.8, 131.7, 130.0, 129.7, 128.4, 123.0, 67.5, 21.7. $^{19}$F NMR (376 MHz, CDCl$_3$) δ −78.9 (s, 3F). HRMS (ESI-TOF): Anal. Calcd. For C$_{16}$H$_{13}$F$_3$O$_6$S$_2$+Na$^+$: 444.9998, Found: 445.0036; IR (neat, cm$^{-1}$): ν 3107, 3072, 2981, 2853, 1693, 1177, 1091, 861, 741, 667.

Example 12

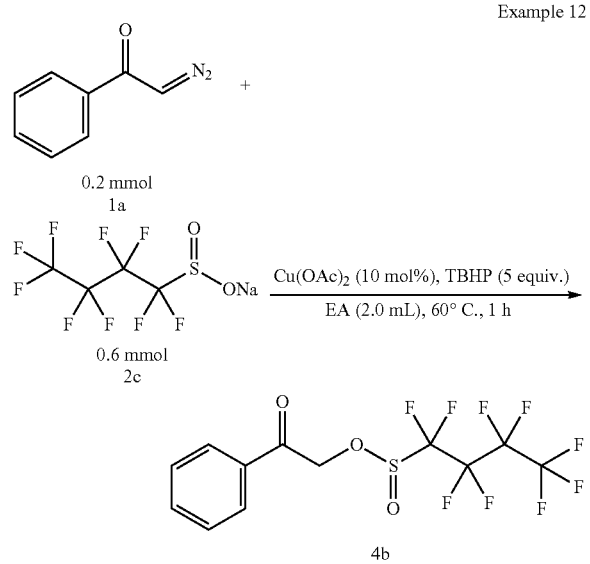

Compound 1a (0.2 mmol, 29.3 mg), 2c (0.6 mmol, 183.7 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 4b, in a yield 63%. The analytical data of the prepared product are as follows. The data of the actual synthetic products are consistent with the theoretical analysis.

$^1$H NMR (400 MHz, CDCl$_3$) δ 7.95-7.85 (m, 2H), 7.68-7.64 (m, 1H), 7.54-7.50 (m, 2H), 5.63 (d, J=16.7 Hz, 1H), 5.34 (d, J=16.7 Hz, 1H). $^{13}$C NMR (100 MHz, CDCl$_3$) δ 191.0, 134.7, 133.2, 129.1, 127.9, 67.5, not all carbons are reported due to extensive $^{19}$F splitting. $^{19}$F NMR (376 MHz, CDCl$_3$) δ −80.8 (t, J=9.5 Hz, 3F), −119.4--121.2 (m, 2F), −122.28--122.32 (m, 2F), −126.1--126.2 (m, 2F). HRMS (ESI-TOF): Anal. Calcd. For C$_{12}$H$_7$F$_9$O$_3$S+Na$^+$: 424.9864, Found: 424.9869; IR (neat, cm$^{-1}$): ν 2930, 2854, 1688, 1226, 951, 758, 684, 676.

Example 13

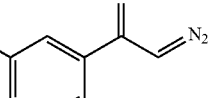

Compound 1m (0.2 mmol, 32.0 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3m, in a yield 66%. The analytical data of the prepared product are as follows. The data of the actual synthetic products are consistent with the theoretical analysis.

$^1$H NMR (400 MHz, CDCl$_3$) δ 7.71-7.67 (m, 2H), 7.48-7.46 (m, 1H), 7.42-7.38 (m, 1H), 5.55 (d, J=16.8 Hz, 1H), 5.36 (d, J=16.8 Hz, 1H), 2.43 (s, 3H). $^{13}$C NMR (100 MHz, CDCl$_3$) δ 191.3, 139.1, 135.4, 133.1, 128.9, 128.3, 125.0, 67.9, 21.2. $^{19}$F NMR (376 MHz, CDCl$_3$) δ −79.0 (s, 3F). HRMS (ESI-TOF): Anal. Calcd. For C$_{10}$H$_9$F$_3$O$_3$S+Na$^+$: 289.0117, Found: 289.0114; IR (neat, cm$^{-1}$): ν 2993, 2946, 2928, 1682, 1170, 970, 779, 708, 686.

Example 14

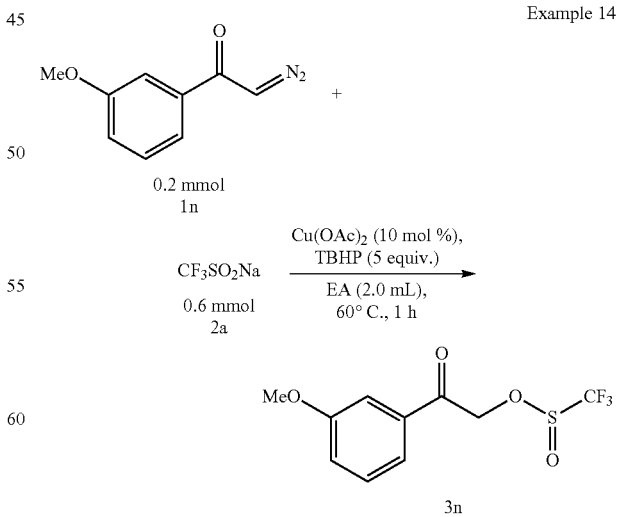

Compound 1n (0.2 mmol, 35.3 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3n, in a yield 67%. The analytical data of the prepared product are as follows. The data of the actual synthetic products are consistent with the theoretical analysis.

$^1$H NMR (400 MHz, CDCl$_3$) δ 7.46-7.38 (m, 3H), 7.23-7.15 (m, 1H), 5.55 (d, J=16.8 Hz, 1H), 5.36 (d, J=16.8 Hz, 1H), 3.86 (s, 3H). $^{13}$C NMR (100 MHz, CDCl$_3$) δ 191.0, 160.1, 134.4, 130.1, 121.2, 120.2, 112.1, 67.9, 55.5. $^{19}$F NMR (376 MHz, CDCl$_3$) δ −79.0 (s, 3F). HRMS (ESI-TOF): Anal. Calcd. For C$_{10}$H$_9$F$_3$O$_4$S+Na$^+$: 305.0066, Found: 305.0080; IR (neat, cm$^{-1}$): ν 3026, 2995, 2840, 1681, 1469, 1172, 860, 781, 682.

Example 15

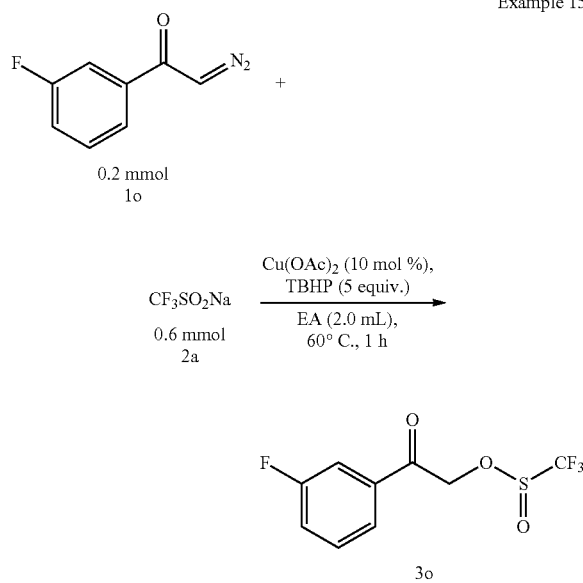

Compound 1o (0.2 mmol, 32.9 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3o, in a yield 56%. The analytical data of the prepared product are as follows. The data of the actual synthetic products are consistent with the theoretical analysis.

$^1$H NMR (400 MHz, CDCl$_3$) δ 7.71-7.65 (m, 1H), 7.64-7.58 (m, 1H), 7.55-7.50 (m, 1H), 7.39-7.35 (m, 1H), 5.54 (d, J=16.8 Hz, 1H), 5.33 (d, J=16.8 Hz, 1H). $^{13}$C NMR (100 MHz, CDCl$_3$) δ 190.0, 162.9 (d, JC-F=249.9 Hz), 135.1 (d, JC-F=6.5 Hz), 131.0 (d, JC-F=7.7 Hz), 123.6 (d, JC-F=3.2 Hz), 121.8 (d, JC-F=21.4 Hz), 114.8 (d, JC-F=22.7 Hz), 67.3. $^{19}$F NMR (376 MHz, CDCl$_3$) δ −78.8 (s, 3F), −110.2 (s, 1F). HRMS (ESI-TOF): Anal. Calcd. For C$_9$H$_6$F$_4$O$_3$S+Na$^+$: 292.9866, Found: 292.9868; IR (neat, cm$^{-1}$): ν 3092, 2921, 2851, 1689, 1176, 1126, 977, 784.

Example 16

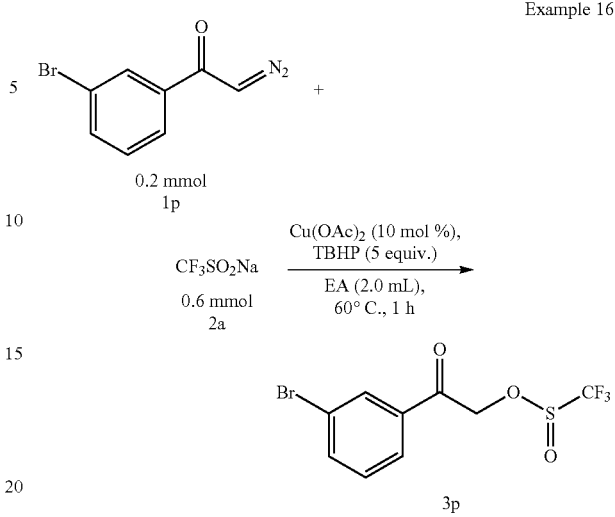

Compound 1p (0.2 mmol, 32.9 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3p, in a yield 75%. The analytical data of the prepared product are as follows. The data of the actual synthetic products are consistent with the theoretical analysis.

$^1$H NMR (400 MHz, CDCl$_3$) δ 8.04-8.03 (m, 1H), 7.86-7.75 (m, 2H), 7.43-7.39 (m, 1H), 5.53 (d, J=16.8 Hz, 1H), 5.33 (d, J=16.8 Hz, 1H). $^{13}$C NMR (100 MHz, CDCl$_3$) δ 190.0, 137.5, 134.8, 130.9, 130.7, 126.3, 123.4, 67.3. $^{19}$F NMR (376 MHz, CDCl$_3$) δ −78.8 (s, 3F). HRMS (ESI-TOF): Anal. Calcd. For C$_9$H$_6$BrF$_3$O$_3$S+Na$^+$: 352.9065, Found: 352.9087; IR (neat, cm$^{-1}$): ν 3095, 2945, 2853, 1691, 1179, 1060, 971, 795.

Example 17

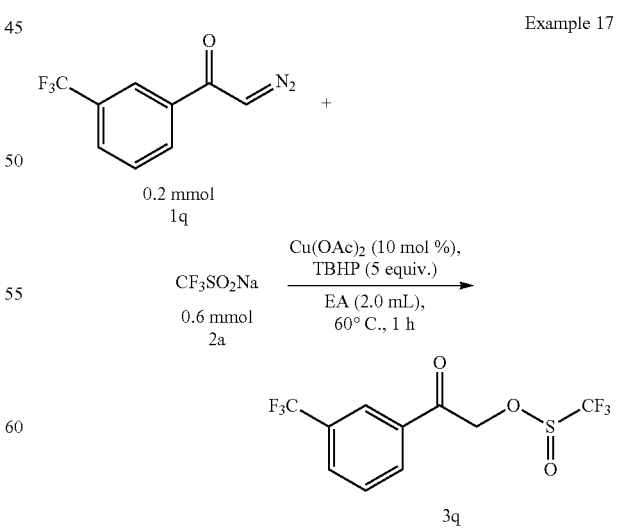

Compound 1q (0.2 mmol, 42.9 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3q, in a yield 68%. The analytical data of the prepared product are as follows. The data of the actual synthetic products are consistent with the theoretical analysis.

$^1$H NMR (400 MHz, CDCl$_3$) δ 8.16 (s, 1H), 8.10 (d, J=7.9 Hz, 1H), 7.92 (d, J=7.9 Hz, 1H), 7.72-7.68 (m, 1H), 5.58 (d, J=16.8 Hz, 1H), 5.38 (d, J=16.8 Hz, 1H). $^{13}$C NMR (100 MHz, CDCl$_3$) δ 190.1, 133.8, 131.9 (q, J=33.3 Hz), 131.0, 130.9, 129.9, 124.8 (q, J=3.8 Hz), 124.7, 67.3. $^{19}$F NMR (376 MHz, CDCl$_3$) δ −63.0 (s, 3F), −78.8 (s, 3F). HRMS (ESI-TOF): Anal. Calcd. For C$_{10}$H$_6$F$_6$O$_3$S+Na$^+$: 342.9834, Found: 342.9839; IR (neat, cm$^{-1}$): ν 3082, 2988, 2943, 1690, 1129, 978, 705, 690.

Example 18

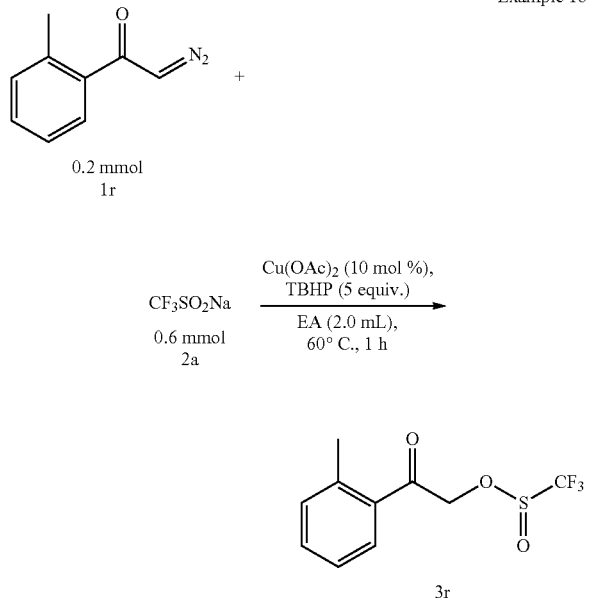

Compound 1r (0.2 mmol, 32.0 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3r, in a yield 73%. The analytical data of the prepared product are as follows. The data of the actual synthetic products are consistent with the theoretical analysis.

$^1$H NMR (400 MHz, CDCl$_3$) δ 7.57 (d, J=7.9 Hz, 1H), 7.50-7.46 (m, 1H), 7.36-7.28 (m, 2H), 5.45 (d, J=16.8 Hz, 1H), 5.24 (d, J=16.8 Hz, 1H), 2.56 (s, 3H). $^{13}$C NMR (100 MHz, CDCl$_3$) δ 193.8, 140.0, 133.1, 132.75, 132.66, 128.3, 126.0, 68.7, 21.4. $^{19}$F NMR (376 MHz, CDCl$_3$) δ −79.1 (s, 3F). HRMS (ESI-TOF): Anal. Calcd. For C$_{10}$H$_9$F$_3$O$_3$S+Na$^+$: 289.0117, Found: 289.0115; IR (neat, cm$^{-1}$): ν 2987, 2930, 1694, 1187, 945, 757, 721, 664.

Example 19

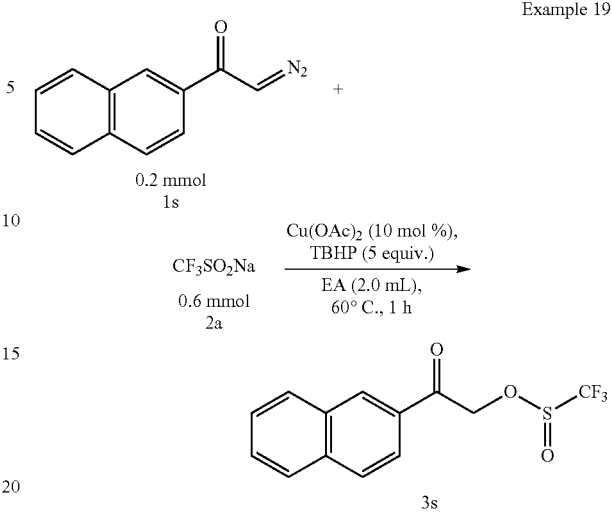

Compound 1s (0.2 mmol, 39.3 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3s, in a yield 52%. The analytical data of the prepared product are as follows. The data of the actual synthetic products are consistent with the theoretical analysis.

$^1$H NMR (400 MHz, CDCl$_3$) δ 8.38 (s, 1H), 8.04-7.85 (m, 4H), 7.68-7.57 (m, 2H), 5.69 (d, J=16.6 Hz, 1H), 5.49 (d, J=16.6 Hz, 1H). $^{13}$C NMR (100 MHz, CDCl$_3$) δ 191.0, 136.1, 132.2, 130.5, 129.9, 129.6, 129.4, 129.2, 127.9, 127.3, 123.0, 67.8. $^{19}$F NMR (376 MHz, CDCl$_3$) δ −78.9 (s, 3F). HRMS (ESI-TOF): Anal. Calcd. For C$_{13}$H$_9$F$_3$O$_3$S+Na$^+$: 325.0017, Found: 325.0019; IR (neat, cm$^{-1}$): ν 3065, 2990, 2942, 1681, 1193, 984, 822, 785, 740, 709.

Example 20

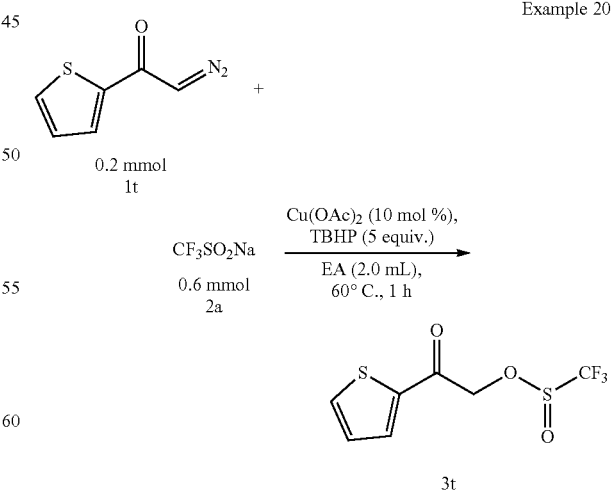

Compound 1t (0.2 mmol, 30.5 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3t, in a yield 63%. The analytical data of the prepared product are as follows. The data of the actual synthetic products are consistent with the theoretical analysis.

$^1$H NMR (400 MHz, CDCl$_3$) δ 7.80-7.77 (m, 2H), 7.22-7.20 (m, 1H), 5.43 (d, J=16.2 Hz, 1H), 5.24 (d, J=16.2 Hz, 1H). $^{13}$C NMR (100 MHz, CDCl$_3$) δ 184.1, 139.2, 135.6, 132.8, 128.6, 67.2. $^{19}$F NMR (376 MHz, CDCl$_3$) δ −78.8 (s, 3F). HRMS (ESI-TOF): Anal. Calcd. For C$_7$H$_5$F$_3$O$_3$S$_2$+Na$^+$: 280.9524, Found: 280.9515; IR (neat, cm$^{-1}$): ν 3095, 2995, 2852, 1656, 1194, 1028, 915, 728, 710.

Example 21

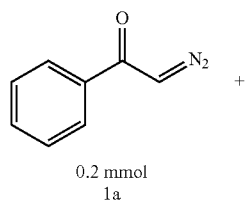

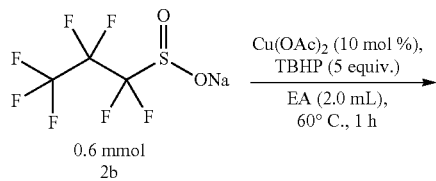

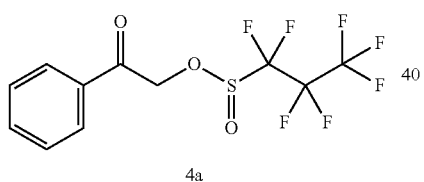

Compound 1a (0.2 mmol, 29.3 mg), 2b (0.6 mmol, 153.7 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 4a, in a yield 68%. The analytical data of the prepared product are as follows. The data of the actual synthetic products are consistent with the theoretical analysis.

$^1$H NMR (400 MHz, CDCl$_3$) δ 7.95-7.84 (m, 2H), 7.68-7.65 (m, 1H), 7.55-7.51 (m, 2H), 5.62 (d, J=16.7 Hz, 1H), 5.35 (d, J=16.7 Hz, 1H). $^{13}$C NMR (100 MHz, CDCl$_3$) δ 191.0, 134.7, 133.1, 129.1, 127.9, 67.5, not all carbons are reported due to extensive $^{19}$F splitting. $^{19}$F NMR (376 MHz, CDCl$_3$) δ −80.9 (t, J=8.5 Hz, 3F), −120.0--121.7 (m, 2F), −125.60--125.63 (m, 2F). HRMS (ESI-TOF): Anal. Calcd. For C$_{11}$H$_7$F$_7$O$_3$S+Na$^+$: 374.9896, Found: 374.9912; IR (neat, cm$^{-1}$): ν 2980, 2943, 1685, 1179, 1046, 947, 721, 687.

Example 22

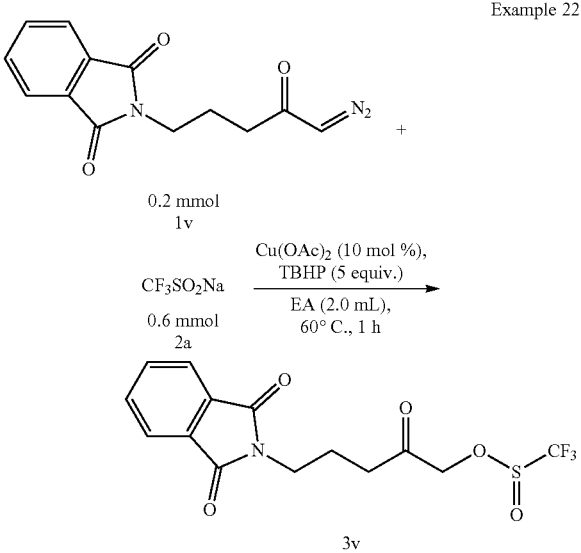

Compound 1v (0.2 mmol, 51.5 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3v, in a yield 63%. The analytical data of the prepared product are as follows. The data of the actual synthetic products are consistent with the theoretical analysis.

$^1$H NMR (400 MHz, CDCl$_3$) δ 7.87-7.81 (m, 2H), 7.77-7.70 (m, 2H), 4.91 (d, J=16.8 Hz, 1H), 4.70 (d, J=16.8 Hz, 1H), 3.73 (t, J=6.4 Hz, 2H), 2.59-2.55 (m, 2H), 2.08-2.00 (m, 2H). $^{13}$C NMR (100 MHz, CDCl$_3$) δ 201.9, 168.5, 134.0, 131.8, 123.2, 69.4, 36.6, 35.6, 21.9. $^{19}$F NMR (376 MHz, CDCl$_3$) δ −78.8 (s, 3F). HRMS (ESI-TOF): Anal. Calcd. For C$_{14}$H$_{12}$F$_3$NO$_5$S+Na$^+$: 386.0280, Found: 386.0276; IR (neat, cm$^{-1}$): ν 2988, 2950, 2886, 1697, 1401, 1367, 965, 720.

Example 23

Compound 1d' (0.2 mmol, 56.9 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3d', in a yield 71%. The analytical data of the prepared product are as follows. The data of the actual synthetic products are consistent with the theoretical analysis.

$^1$H NMR (400 MHz, CDCl$_3$) δ 7.79 (d, J=8.3 Hz, 2H), 7.37 (d, J=8.0 Hz, 2H), 4.79 (d, J=16.4 Hz, 1H), 4.57 (d, J=16.4 Hz, 1H), 4.42-4.39 (m, 2H), 4.28-4.25 (m, 2H), 2.46 (s, 3H). $^{13}$C NMR (100 MHz, CDCl$_3$) δ 166.3, 145.3, 132.5, 130.0, 127.9, 66.8, 63.1, 61.7, 21.6. $^{19}$F NMR (376 MHz, CDCl$_3$) δ −78.7 (s, 3F). HRMS (ESI-TOF): Anal. Calcd. For C$_{12}$H$_{13}$F$_3$O$_7$S$_2$+Na$^+$: 412.9947, Found: 412.9970; IR (neat, cm$^{-1}$): ν 2958, 2924, 2852, 1759, 1173, 1127, 815, 769.

Example 24

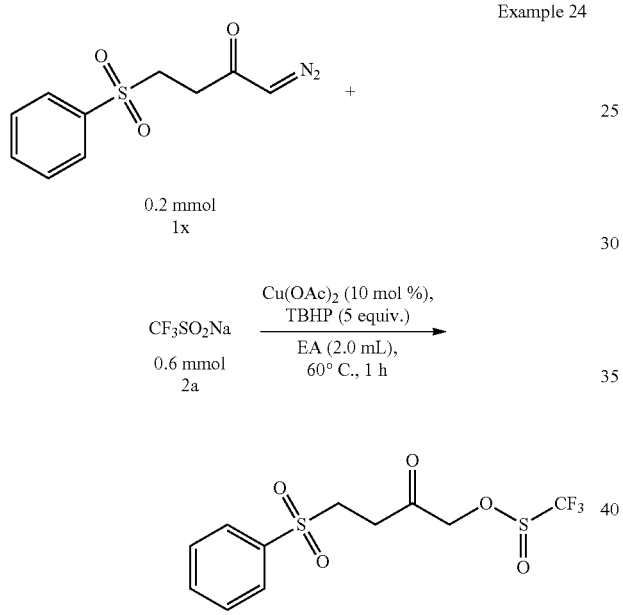

Compound 1x (0.2 mmol, 47.7 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3x, in a yield 52%. The analytical data of the prepared product are as follows. The data of the actual synthetic products are consistent with the theoretical analysis.

$^1$H NMR (400 MHz, CDCl$_3$) δ 7.95-7.87 (m, 2H), 7.76-7.67 (m, 1H), 7.62-7.59 (m, 2H), 4.91 (d, J=16.8 Hz, 1H), 4.64 (d, J=16.8 Hz, 1H), 3.47-3.43 (m, 1H), 3.01 (t, J=7.2 Hz, 1H). $^{13}$C NMR (100 MHz, CDCl$_3$) δ 199.1, 138.5, 134.2, 129.6, 128.0, 68.4, 49.9, 31.8. $^{19}$F NMR (376 MHz, CDCl$_3$) δ −78.3 (s, 3F). HRMS (ESI-TOF): Anal. Calcd. For C$_{11}$H$_{11}$F$_3$O$_5$S$_2$+Na$^+$: 366.9892, Found: 366.9896; IR (neat, cm$^{-1}$): ν 3066, 2998, 2849, 1737, 1188, 968, 738, 686.

Example 25

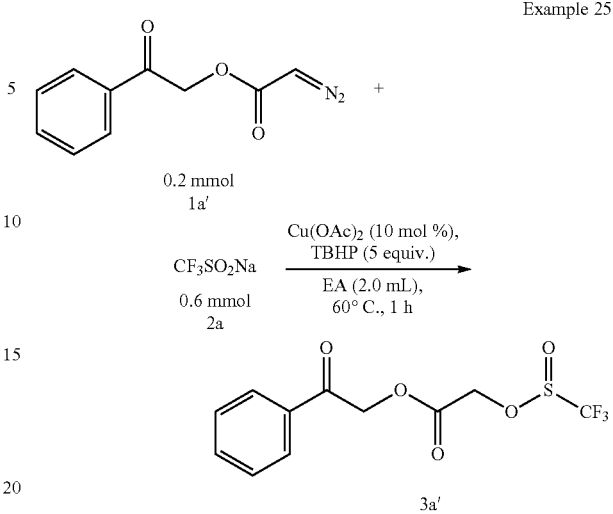

Compound 1a' (0.2 mmol, 40.9 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3a', in a yield 70%. The analytical data of the prepared product are as follows. The data of the actual synthetic products are consistent with the theoretical analysis.

$^1$H NMR (400 MHz, CDCl$_3$) δ 7.91-7.89 (m, 2H), 7.68-7.57 (m, 1H), 7.53-7.49 (m, 2H), 5.54-5.43 (m, 2H), 5.05 (d, J=16.4 Hz, 1H), 4.85 (d, J=16.4 Hz, 1H). $^{13}$C NMR (100 MHz, CDCl$_3$) δ 190.5, 166.3, 134.3, 133.6, 129.0, 127.7, 67.0, 61.9. $^{19}$F NMR (376 MHz, CDCl$_3$) δ −78.7 (s, 3F). HRMS (ESI-TOF): Anal. Calcd. For C$_{11}$H$_9$F$_3$O$_5$S+Na$^+$: 333.0015, Found: 333.0020; IR (neat, cm$^{-1}$): ν 3006, 2973, 2938, 1747, 1692, 1171, 755, 716, 686.

Example 26

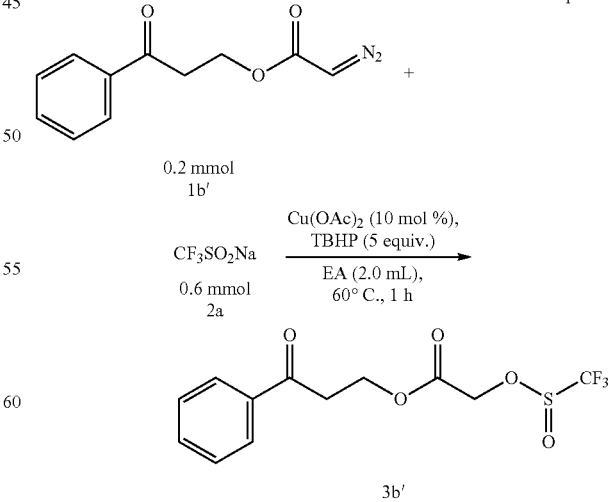

Compound 1b' (0.2 mmol, 40.9 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3b', in a yield 57%. The analytical data of the prepared product are as follows. The data of the actual synthetic products are consistent with the theoretical analysis.

$^1$H NMR (400 MHz, CDCl$_3$) δ 7.96-7.94 (m, 2H), 7.63-7.57 (m, 1H), 7.52-7.46 (m, 2H), 4.82 (d, J=16.2 Hz, 1H), 4.69 (t, J=6.2 Hz, 2H), 4.61 (d, J=16.2 Hz, 1H), 3.37 (t, J=6.2 Hz, 2H). $^{13}$C NMR (100 MHz, CDCl$_3$) δ 196.2, 166.6, 136.2, 133.6, 128.7, 128.0, 62.0, 61.2, 36.9. $^{19}$F NMR (376 MHz, CDCl$_3$) δ −78.7 (s, 3F). HRMS (ESI-TOF): Anal. Calcd. For C$_{14}$H$_{13}$F$_3$O$_3$S+Na$^+$: 347.0171, Found: 347.0175; IR (neat, cm$^{-1}$): ν 2970, 2926, 1750, 1683, 1191, 1126, 1033, 689.

Example 27

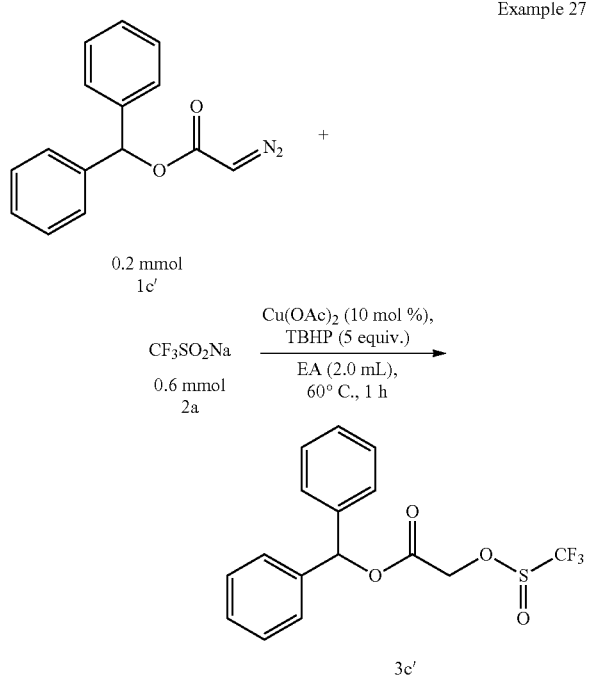

Compound 1c' (0.2 mmol, 50.5 mg), 2a (0.6 mmol, 101.8 mg), Cu(OAc)$_2$ (0.02 mmol, 3.7 mg), ethyl acetate EA (2.0 mL), TBHP (1.0 mmol, 139 μL) were added to a reactor and then heated and stirred at 60° C. in the air for 1 hour. The reaction mixture was directly diluted with 2.0 mL of ethyl acetate. The solvent was removed by rotary evaporator, and silica gel column chromatography was carried out to obtain product 3c', in a yield 67%. The analytical data of the prepared product are as follows. The data of the actual synthetic products are consistent with the theoretical analysis.

$^1$H NMR (400 MHz, CDCl$_3$) δ 7.38-7.27 (m, 10H), 6.99 (s, 1H), 4.91 (d, J=16.2 Hz, 1H), 4.69 (d, J=16.2 Hz, 1H). $^{13}$C NMR (100 MHz, CDCl$_3$) δ 165.7, 138.83, 138.78, 128.7, 128.4, 127.10, 127.06, 78.9, 62.2. $^{19}$F NMR (376 MHz, CDCl$_3$) δ −78.7 (s, 3F). HRMS (ESI-TOF): Anal. Calcd. For C$_{16}$H$_{13}$F$_3$O$_4$S+Na$^+$: 381.0379, Found: 381.0376; IR (neat, cm$^{-1}$): ν 3065, 3033, 2987, 1751, 1181, 1029, 743, 696.

The invention claimed is:
1. A method for preparing a perfluoroalkylsulfinate ester, comprising:
  reacting an α-carbonyldiazo compound with a sodium perfluoroalkylsulfinate in the presence of a transition metal compound as a catalyst, with a peroxide as an oxidant, in an organic solvent, to obtain the perfluoroalkylsulfinate ester,
  wherein the α-carbonyldiazo compound has the following chemical structural formula:

R$_1$ is selected from the group consisting of naphthyl, thienyl, alkyl, alkoxy, and phenol; or R$_1$ is R$_2$ is selected from the group consisting of hydrogen, methyl, ethyl, tert-butyl, methoxy, phenyl, fluorine, chlorine, bromine, trifluoromethyl, hydroxyl, acetoxy, and p-toluenesulfonyloxy;
  wherein the sodium perfluoroalkylsulfinate is wherein the transition metal compound is selected from the group consisting of a copper compound, a cobalt compound, and an iron compound;
  wherein the peroxide is hydrogen peroxide or tert-butyl hydroperoxide (TBHP); and
  wherein the perfluoroalkylsulfinate ester has the following chemical structural formula:

n is 1 to 8.

2. The method according to claim 1, wherein the reaction of the α-carbonyldiazo compound with the sodium perfluoroalkylsulfinate is conducted at 50 to 90° C., for 1 to 6 hours, in the air; the transition metal compound is a copper compound; the organic solvent is petroleum ether, 1,2-dichloroethane, 1,1,1-trichloroethane, 1,1,2-trichloroethane, nitro methane, acetonitrile, or ethyl acetate.

3. The method according to claim 2, wherein the reaction is conducted at 60° C., in the air, for 1 hour; the copper compound is anhydrous copper acetate; and the organic solvent is ethyl acetate.

4. The method according to claim 3, further comprising after the reaction is complete, diluting with ethyl acetate, removing ethyl acetate, and conducting silica column chromatography to obtain the perfluoroalkylsulfinate ester.

5. The method according to claim 1, wherein a molar ratio of the catalyst to the α-carbonyldiazo compound is 1:10; a molar ratio of the oxidant to the α-carbonyldiazo compound is 5:1; and a molar ratio of the sodium perfluoroalkylsulfinate to the α-carbonyldiazo compound is 3:1.

\* \* \* \* \*